(12) United States Patent
Rosengard

(10) Patent No.: US 6,982,156 B2
(45) Date of Patent: *Jan. 3, 2006

(54) COMPOSITIONS AND METHODS MODULATING VARIOLA AND VACCINIA VIRUS

(75) Inventor: Ariella M. Rosengard, Gladwyne, PA (US)

(73) Assignee: Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/441,624

(22) Filed: May 20, 2003

(65) Prior Publication Data
US 2005/0129700 A1 Jun. 16, 2005

Related U.S. Application Data

(63) Continuation-in-part of application No. 10/108,311, filed on Mar. 27, 2002, now Pat. No. 6,783,759.

(51) Int. Cl.
A61K 39/42 (2006.01)
A61K 39/395 (2006.01)

(52) U.S. Cl. .............................. 435/159.1; 435/139.1; 435/147.1; 530/387.9; 530/388.3; 530/389.4

(58) Field of Classification Search .............. 424/139.1, 424/147.1, 159.1, 232.1; 530/387.9, 388.3, 530/389.4
See application file for complete search history.

(56) References Cited

U.S. PATENT DOCUMENTS 5,157,110 A 10/1992 Kotwal et al. ............... 530/350
5,843,778 A 12/1998 Rosengard et al. .......... 435/325

FOREIGN PATENT DOCUMENTS

WO WO 93/19183 9/1993
WO WO 95/20660 8/1995
WO WO 99/44625 9/1999

OTHER PUBLICATIONS

"Vaccinia (Smallpox) Vaccine Recommendations of the Immunization Practices Advisory Committee (ACIP)." MMWR 40(RR14):1-10, 1991.*
Campbell et al., Methods and Immunology, W.A. Benjamin, Inc. 1964.
Cooper N.R., "Complement and Viruses", The Human Complement System in Health and Disease, vol. 1, Editors Volanakis J.E. and Frank M.M. 393-407 Marcel Dekker, Inc. New York 1998.
Conry et al., "Immune Response to a Carcinoembryonic Antigen Polynucleotide Vaccine", Cancer Research 1994 54:1164-1168.
Cox et al., "Bovine Herpesvirus 1:Immune Responses in Mice and Cattle Injected with Plasmid DNA", Virology 1993 67(9): 5664-5667.
Dalmasso A.P., "Role of Complement in Graft Rejection", In:The Complement System, vol. 1 (editors Rother, K., Till, G.O., & Hänsch, G.M.) Springer-Verlag, Berlin 1997 471-486.
Davis et al., "DNA-based immunization induces continuous secretion of hepatitis B surface antigen and high levels of circulating antibody", Human Molecular Genetics 1993 2 (11):1847-1851.
DePraval et al., "Variability of Interchain Binding of Immunoglobulins" Nature 1970 228:930-932.
Dempsey et al., "C3d of Complement as a Molecular Adjuvant:Bridging Innate and Acquired Immunity", Science 1996 271:348-350.
Donnelly et al., "Preclinical efficacy of a prototype DNA vaccine:Enhanced protection against antigenic drift in influenza virus", Nature Medicine 1995 1 (6) : 583-587.
ELISA in Methods of Immunodiagnosis, 2nd Edition, Rose and Bigazzi, editors John Wiley & Sons 1980.
Fynan et al., "Use of DNA Encoding Influenza Hemagglutinin as an Avian Influenza Vaccine", DNA and Cell Biology 1993 12(9):785-789.
Fynan et al., "DNA vaccines: Protective immunizations by parenteral, mucosal, and gene-gun inoculations", Proc. Natl. Acad. Sci. USA 1993 90:11478-11482.
Harlow and Lane—Antibodies: A Laboratory Manual—Cold Spring Harbor Laboratory, New York 1988 Chapter 14 553-612.
Isaacs et al., "Vaccinia virus complement-control protein prevents antibody-dependent complement-enhanced neutralization of infectivity and contributes to virulence", Proc. Natl. Acad. Sci. USA 1992 89:628-632.
Kalli et al., "Mapping of the C3b-binding Site of CR1 and Construction of a $(CR1)_2$-F(ab') $_2$ Chimeric Complement Inhibitor", J. Exp. Med 1991 174:1451-1460.
Kennedy et al., "Protein-Protein Coupling Reactions and the Applications of Protein Conjugates", Clinica Chimica Acta 1976 70:1-31.

(Continued)

Primary Examiner—Mary E. Mosher
(74) Attorney, Agent, or Firm—Licata & Tyrrell P.C.

(57) ABSTRACT

Antibodies directed to SPICE and VCP which may be used for detection, prevention, and treatment of variola virus or vaccinia virus are provided. Recombinant SPICE and VCP proteins are also provided which are used for enhancing the immune response to variola or vaccinia virus and modulating of complement activation. Methods and kits for detecting nucleic acid sequences encoding SPICE and VCP are also provided.

2 Claims, 1 Drawing Sheet

OTHER PUBLICATIONS

Khaw et al., "Radiochemistry and Radiopharmaceuticals—Technetium-99m Labeling of Antibodies to Cardiac Myosin Fab and to Human Fibrinogen", J. Nucl. Med. 1982 1011-1019.

Kitamura H., "Interspecies Incomatibilities of Complement Factors and Regulators", In:The Complement System, vol. 1 (editors Rother, K., Till, G.O., & Hänsch, G.M.) Springer-Verlag, Berlin 1998.

Klickstein et al., "Identification of Distinct C3b and C4b Recogntiion Sites in the Human C3b/C4b Receptor (CR1, CD35) by Deletion Mutagenesis", J. Exp. Med. 1988 168: 1699-1711.

Köhler and Mulstein, "Continuous cultures of fused cells secreting antibody of predefined specificity", Nature 1975 256:495-497.

Kotwal et al., "Vaccinia virus encodes a secretory polypeptide structurally related to complement control proteins", Nature 1988 335:176-178.

Kotwal et al., "Inhibition of the Complement Cascade by the Major Secretory Protein of Vaccinia Virus", Science 1990 250:827-830.

Krych et al., "Analysis of the Functional Domains of Complement Receptor Type 1 (C3b/C4b Receptor; CD35) by Substitution Mutagenesis", J. Biol. Chem. 1994 269: 13273-13278.

Krych et al., "Sites within the complement C3b/C4b receptor important for the specificity of ligand binding", Proc. Natl. Acad. Sci. USA 1991 88:4353-4357.

Lachmann et al., "Complement and immunity to viruses", Immunological Reviews 1997 159:69-77.

Lachmann P.J., "Microbial subversion of the immune response", PNAS 2002 99(13):8461-8462.

Liszewski et al., "Regulatory Proteins of Complement" In:The Human Complement System in Health and Disease vol. 1 Editors Volanakis J.E. and Frank M.M. Marcel Dekker, Inc. New York 1998 149-166.

Massung et al., "Terminal Region Sequence Variations in Variola Virus DNA", Virology 1996 221:291-300.

McKenzie et al., "Regulation of Complment Activity by Vaccinia Virus Complement-Control Protein", J. Infect. Dis. 1992 166:1245-1250.

McPherson et al., PCR, A Practical Approach, IRL Press, Oxford, England 1991.

Montgomery et al., "Heterologous and Homologous Protection Agaisnt Influenza A by DNA Vaccination:Optimization of DNA Vectors", DNA Cell Biol. 1993 12(9):777-783.

Moss B., "Genetically engineered poxviruses for recombinant gene expression, vaccination, and safety", Proc. Natl. Acad. Sci. USA 1996 93:11341-11348.

Mroczkowski et al., "Secretion of Thermostable DNA Polymerase Using a Novel Baculovirus Vector", J. Biol. Chem. 1994 269(18):13522-13528.

Pangburn et al., "Human Complement C3b Inactivator: Isolation, Characterization, and Demonstration of an Absolute Requirement for the Serum Protein β1H for Cleavage of C3b and C4b in Solution", J. Exp. Med. 1977 146:257-270.

Raz et al., "Intradermal gene immunization:The possible role of DNA uptake in the induction of cellular immunity to viruses", Proc. Natl. Acad. Sci. USA 1994 91:9519-9523.

Remington's Pharmaceutical Sciences 16th edition Osol A., Editor Mack Easton, PA 1980.

Robinson et al., "Protection against a lethal influenza virus challenge by immunization with a haemagglutinin-expressing plasmid DNA", Vaccine 1993 11:957-960.

Ropp et al., "PCR Strategy for Identification and Differentiation of Smallpox and Other Orthopoxviruses", J. Clin. Microbiol. 1995 33(8):2069-2076.

Rosengard et al., "Functional characterization of soluble and membrane-bound forms of vaccinia virus complement control protein (VCP)", Mol. Immunol. 1999 36:689-697.

Rosengard et al., "Variola virus immune evasion design: Expression of a highly efficient inhibitor of human complement", PNAS 2002 99(13):8803-8813.

Ross et al., "C3d enhancement of antibodies to hemagglutinin accelerates protection against influenza virus challenge", Nat. Immunol. 2000 1(2):127-131.

Ross et al., "Generation of Three Different Fragments of Bound C3 with Purified Factor 1 or Serum", J. Immunol. 1982 129(5):2051-2060.

Sahu et al., "Interaction of Vaccinia Virus Complement Control Protein with Human Complement Proteins:Factor I-Mediated Degradation of C3b to $iC3b_1$ Inactivates the Alternative Complement Pathway1", J. Immunol. 1998 160: 5596-5604.

Schuurs et al., "Enzyme-Immunoassay", Clin. Chim. Acta 1977 81:1-40.

Shchelkunov et al., "Genes of variola and vaccinia viruses necessary to overcome the host protective mechanisms", FEBS Lett. 1993 319:80-83.

Sedegah et al., "Protection against malaria by immunization with plasmid DNA encoding circumsporozoite protein", Proc. Natl. Acad. Sci. USA 1994 91:9866-9870.

Ulmer et al., "Heterologous Protection Against Influenza by Injection of DNA Encoding a Viral Protein", Science 193 259:1745-1749.

Wang et al., "Gene inoculation generates immuine responses against human immunodeficiency virus type 1", Proc. Natl. Acad. Sci. USA 1993 90:4156-4160.

Webster et al., "Protection of ferrets against influenza challenge with a DNA vaccine to the hemagglutinin", Vaccine 1994 12:1495-1498.

Weisman et al., "Soluble Human Complement Receptor Type 1:In Vivo Inhibitor of Complement Suppressing Post-Ischemic Myocardial Inflammation and Necrosis", Science 249:146-151.

Xiang et al., "Vaccination iwth a Plasmid Vector Carrying the Rabies Virus Glycoprotein Gene Induces Protective Immunity against rabies Virus", Virology 1994 199:132-140.

Yankauckas et al., "Long-Term Anti-Nucleoprotein Cellular and Humoral Immunity Is Intramuscular Injection of Plasmid DNA Containing NP Gene", DNA Cell Biol. 1993 12:771-776.

* cited by examiner

SEQUENCE LISTING

<160> NUMBER OF SEQ ID NOS: 13

<210> SEQ ID NO 1

```
<211> LENGTH: 66
<212> TYPE: PRT
<213> ORGANISM: Variola virus

<400> SEQUENCE: 1

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg
65

<210> SEQ ID NO 2
<211> LENGTH: 66
<212> TYPE: PRT
<213> ORGANISM: Vaccinia virus

<400> SEQUENCE: 2

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg
65

<210> SEQ ID NO 3
<211> LENGTH: 62
<212> TYPE: PRT
<213> ORGANISM: Variola virus

<400> SEQUENCE: 3

Cys Pro Ser Pro Arg Asp Ile Asp Asn Gly His Leu Asp Ile Gly Gly
1               5                   10                  15

Val Asp Phe Gly Ser Ser Ile Thr Tyr Ser Cys Asn Ser Gly Tyr Tyr
            20                  25                  30

Leu Ile Gly Glu Tyr Lys Ser Tyr Cys Lys Leu Gly Ser Thr Gly Ser
        35                  40                  45

Met Val Trp Asn Pro Lys Ala Pro Ile Cys Glu Ser Val Lys
    50                  55                  60

<210> SEQ ID NO 4
<211> LENGTH: 62
<212> TYPE: PRT
<213> ORGANISM: Vaccinia virus

<400> SEQUENCE: 4

Cys Pro Ser Pro Arg Asp Ile Asp Asn Gly Gln Leu Asp Ile Gly Gly
1               5                   10                  15

Val Asp Phe Gly Ser Ser Ile Thr Tyr Ser Cys Asn Ser Gly Tyr His
            20                  25                  30

Leu Ile Gly Glu Ser Lys Ser Tyr Cys Glu Leu Gly Ser Thr Gly Ser
```

```
                35                  40                  45
Met Val Trp Asn Pro Glu Ala Pro Ile Cys Glu Ser Val Lys
        50                  55                  60

<210> SEQ ID NO 5
<211> LENGTH: 57
<212> TYPE: PRT
<213> ORGANISM: Variola virus

<400> SEQUENCE: 5

Cys Gln Leu Pro Pro Ser Ile Ser Asn Gly Arg His Asn Gly Tyr Asn
1               5                   10                  15

Asp Phe Tyr Thr Asp Gly Ser Trp Thr Tyr Ser Cys Asn Ser Gly Tyr
            20                  25                  30

Ser Leu Ile Gly Asn Ser Gly Val Leu Cys Ser Gly Gly Glu Trp Ser
        35                  40                  45

Asn Pro Pro Thr Cys Gln Ile Val Lys
    50                  55

<210> SEQ ID NO 6
<211> LENGTH: 57
<212> TYPE: PRT
<213> ORGANISM: Vaccinia virus

<400> SEQUENCE: 6

Cys Gln Ser Pro Pro Ser Ile Ser Asn Gly Arg His Asn Gly Tyr Glu
1               5                   10                  15

Asp Phe Tyr Thr Asp Gly Ser Trp Thr Tyr Ser Cys Asn Ser Gly Tyr
            20                  25                  30

Ser Leu Ile Gly Asn Ser Gly Val Leu Cys Ser Gly Gly Glu Trp Ser
        35                  40                  45

Asp Pro Pro Thr Cys Gln Ile Val Lys
    50                  55

<210> SEQ ID NO 7
<211> LENGTH: 58
<212> TYPE: PRT
<213> ORGANISM: Variola virus

<400> SEQUENCE: 7

Cys Pro His Pro Thr Ile Leu Asn Gly Tyr Leu Ser Ser Gly Phe Lys
1               5                   10                  15

Arg Ser Tyr Ser Tyr Asn Asp Asn Val Asp Phe Thr Cys Lys Tyr Gly
            20                  25                  30

Tyr Lys Leu Ser Gly Ser Ser Ser Thr Cys Ser Pro Gly Asn Thr
        35                  40                  45

Trp Gln Pro Glu Leu Pro Lys Cys Val Arg
    50                  55

<210> SEQ ID NO 8
<211> LENGTH: 58
<212> TYPE: PRT
<213> ORGANISM: Vaccinia virus

<400> SEQUENCE: 8

Cys Pro His Pro Thr Ile Ser Asn Gly Tyr Leu Ser Ser Gly Phe Lys
1               5                   10                  15

Arg Ser Tyr Ser Tyr Asn Asp Asn Val Asp Phe Lys Cys Lys Tyr Gly
            20                  25                  30
```

-continued

```
Tyr Lys Leu Ser Gly Ser Ser Ser Thr Cys Ser Pro Gly Asn Thr
        35                  40                  45

Trp Lys Pro Glu Leu Pro Lys Cys Val Arg
    50                  55

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide primer.

<400> SEQUENCE: 9
gcacccggga gttctatcat gctgtactat tccg                           34

<210> SEQ ID NO 10
<211> LENGTH: 56
<212> TYPE: DNA
<213> ORGANISM: Artificial Sequence
<220> FEATURE:
<223> OTHER INFORMATION: Synthetic oligonucleotide primer.

<400> SEQUENCE: 10
gctctagact cgagctagtg gtggtggtgg tggtggcgta cacattttgg aagttc    56

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide primer.

<400> SEQUENCE: 11
gaagatcttt gtactattcc gtcacgaccc attaat                         36

<210> SEQ ID NO 12
<211> LENGTH: 36
<212> TYPE: DNA
<213> ORGANISM: Artificial Sequence
<220> FEATURE:
<223> OTHER INFORMATION: Synthetic oligonucleotide primer.

<400> SEQUENCE: 12
ctagctagcg cgtacacatt ttggaagttc cggctt                         36

<210> SEQ ID NO 13
<211> LENGTH: 37
<212> TYPE: DNA
<213> ORGANISM: Artificial Sequence
<220> FEATURE:
<223> OTHER INFORMATION: Synthetic oligonucleotide primer.

<400> SEQUENCE: 13
aaatcgtatt gtgaattagg atctactgga tctatgg                        37
```

COMPOSITIONS AND METHODS MODULATING VARIOLA AND VACCINIA VIRUS

This application is a continuation-in-part of U.S. patent application Ser. No. 10/108,311, filed Mar. 27, 2002 now U.S. Pat. No. 6,783,759 which is incorporated herein by reference in its entirety.

BACKGROUND OF THE INVENTION

Variola virus, the most virulent member of the genus Orthopoxvirus, specifically infects humans. Variola causes smallpox, which has a 30–40% mortality. Protocols for vaccination rely on the vaccinia virus, which has multiple potential side effects. The United States stopped vaccinating the public against smallpox in 1972, while worldwide vaccination terminated in the late 1970s. Only 10–20% of individuals previously vaccinated are still protected due to waning immunity. Public health concerns regarding the re-emergence of variola virus have led to renewed interest in the pathogenesis of smallpox. Since ethical and public health concerns preclude in vivo work on variola virus, and the World Health Organization prohibits DNA recombination studies between variola DNA fragments and other Orthopoxvirus genomes, studies of variola require indirect approaches. In vivo model systems involving orthopoxviruses do exist but are limited primarily to vaccinia, cowpox, and ectromelia viruses. The relative benign nature of other orthopoxviruses in humans may underestimate the importance of any homologous protein in the pathogenesis of smallpox.

Protocols for resuming the administration of smallpox vaccine, i.e., vaccinia virus, also have serious implications. In the last decades, the growing number of immunocompromised patients suffering from AIDS, cancer and other immunocompromising medical conditions has increased. In addition, the widespread use of immunosuppressants for organ transplant patients, the common practice of radiation and chemotherapy for treating malignancies, as well as the growing size of the aging population have also increased. Administration of the current smallpox vaccine and subsequent shedding of this virus may result in vaccinia virus infections in the population of immunocompromised individuals. Therefore, alternative smallpox vaccines or approaches to attenuate the existing vaccine are imperative at this time.

Complement regulatory proteins (CRPs), encoded by genes located in the terminal regions of orthopoxviruses, are important for viruses to evade a host-mediated complement attack (Cooper, N. R. Complement and Viruses. In: The Human complement System in Health and Disease, Vol. 1 (eds. Volanakis, J. E. & Frank, M. M.) 393–407, Marcel Dekker, Inc. NY, 1998). Virally-encoded CRPs deflect complement destruction of infected host cells and viral particles to allow for more efficient viral spread (Shchelkunov et al. (1993) *FEBS Lett.* 319:80–83; Lachmann and Davies (1997) *Immunological Reviews* 159:69–77). CRPs differ with respect to ligand specificity (C3b and/or C4b) and the mechanism of convertase inactivation. They may accelerate the normal decay of the classical and alternative pathway convertases or function as cofactors for the serine protease factor I, to enzymatically cleave the α' chains of C3b and C4b into smaller, inactive fragments (Liszewski and Atkinson. Regulatory Proteins of Complement. In: The Human complement System in Health and Disease, Vol. 1 (eds. Volanakis, J. E. & Frank, M. M.) 149–166, Marcel Dekker, Inc. NY, 1998). Structurally, CRPs are composed of 4–56 homologous motifs termed short consensus repeats (SCR).

Vaccinia Virus Complement Control Protein (VCP) is a CRP encoded by vaccinia virus that has been shown to enhance the virulence of vaccinia in rabbit and guinea pig experimental models and causes larger lesions when injected intradermally (Isaacs et al. (1992) *Proc. Natl. Acad. Sci. USA* 89:628–632). VCP functions primarily as a cofactor for factor I rather than as a decay accelerator (Kotwal et al. (1990) *Science* 250:827–830; McKenzie et al. (1992) *J. Infect. Dis.* 166:1245–1250; Sahu et al. (1998) *J. Immunol.* 160:5596–5604). U.S. Pat. No. 5,157,110 describes the use of VCP to bind to C4b and inhibit the complement cascade. Furthermore, U.S. Pat. No. 5,843,778 discloses the use of recombinant VCP-immunoglobulin Fc region fusion protein to modulate complement activation through binding of complement components C3b and C4b.

DNA comparison studies revealed that the genomes of all variola virus strains also encode a CRP homolog consisting of four SCRs (Massung et al. (1996) *Virology* 221:291–300). This Smallpox Inhibitor of Complement Enzymes (SPICE) differs from the VCP amino acid sequence by 4.6%; the 11 amino acid differences are dispersed throughout SCR2, SCR3 and SCR4. WO 99/44625 discloses a SPICE polypeptide that has been generated by molecular engineering of VCP. The intended use of this SPICE protein, fused to an immunoglobulin molecule, is to modulate complement activation. Recombinant SPICE differs from VCP protein in that it is 100-fold more potent than VCP at inactivating human C3b and is more human complement-specific than is VCP (Rosengard et al. (2002) *Proc. Natl. Acad. Sci. USA* 99(13): 8808–13).

Few options exist for the rapid detection of smallpox infection. Ropp et al. ((1995) *J. Clin. Microbiol.* 33:2069–76) demonstrate the use of a combined PCR amplification-endonuclease digestion of the hemagglutinin gene to identify and differentiate smallpox from other orthopoxviruses. Moreover, U.S. patent application Ser. No. 09/781,124 describes the use of monoclonal antibodies directed to vaccinia L1 R and A33R antigens to detect, prevent, and/or treat vaccinia virus infections in vitro and in vivo. Monoclonal antibodies directed to orthopoxvirus homologs of vaccinia L1R and A33R antigens are also taught.

The present invention addresses the need for improved detection, prevention, and treatment of variola and vaccinia virus infections. Antibodies directed against SPICE and VCP proteins and SPICE and VCP-specific primers for PCR amplification of the SPICE and VCP genes are provided for the detection of variola or vaccinia virus. The present invention also addresses the need for improved vaccines for the prevention of variola and vaccinia virus infections by providing antibodies directed against SPICE/VCP for passive vaccination. Furthermore, the present invention provides SPICE fusion proteins for vaccination against smallpox virus. Treatment for variola or vaccinia virus infections is provided through administration of an antibody directed against SPICE/VCP. Finally, SPICE fusion proteins are described for binding human complement components to modulate complement activation.

SUMMARY OF THE INVENTION

One aspect of the present invention is antibodies against Smallpox Inhibitor of Complement Enzyme (SPICE) or Vaccinia Virus Complement Control Protein (VCP). The antibodies of the invention may be produced by immunizing an animal with VCP and identifying the antibodies, which specifically cross-react with SPICE or VCP. These antibodies are useful alone or in a pharmaceutical composition for preventing or treating variola or vaccinia virus infection. These antibodies are further useful for preventing side effects associated with vaccinia virus vaccination and may be used for detecting the presence of SPICE or VCP in a sample.

Another aspect of the present invention is directed to nucleic acid sequences encoding SPICE or VCP as DNA vaccines and for detecting the presence of SPICE or VCP in a sample. Methods of administering nucleic acid sequences encoding SPICE or VCP to prevent or treat variola or vaccinia virus infection are provided. Further, primers located 5' and 3' of a SspI sited of the SCR4 region of SPICE may be used to amplify nucleic acid sequences encoding VCP or SPICE from the DNA of a sample. The nucleic acid sequences are restricted with SspI and the presence of restricted fragments are detected. Kits for detecting nucleic acid sequences encoding SPICE or VCP are also provided.

A further aspect of the present invention is a vaccine for the prevention of variola or vaccinia virus infection containing SPICE or VCP or derivatives or fusion proteins thereof or nucleic acid sequences encoding SPICE or VCP.

A still further aspect of the present invention is a method of modulating complement activation by administering a fusion protein of a complement regulatory protein and a tag. In preferred embodiments, the tag is polyhistidine and the complement regulatory protein is SPICE or VCP.

DETAILED DESCRIPTION OF THE INVENTION

Figure 1A:
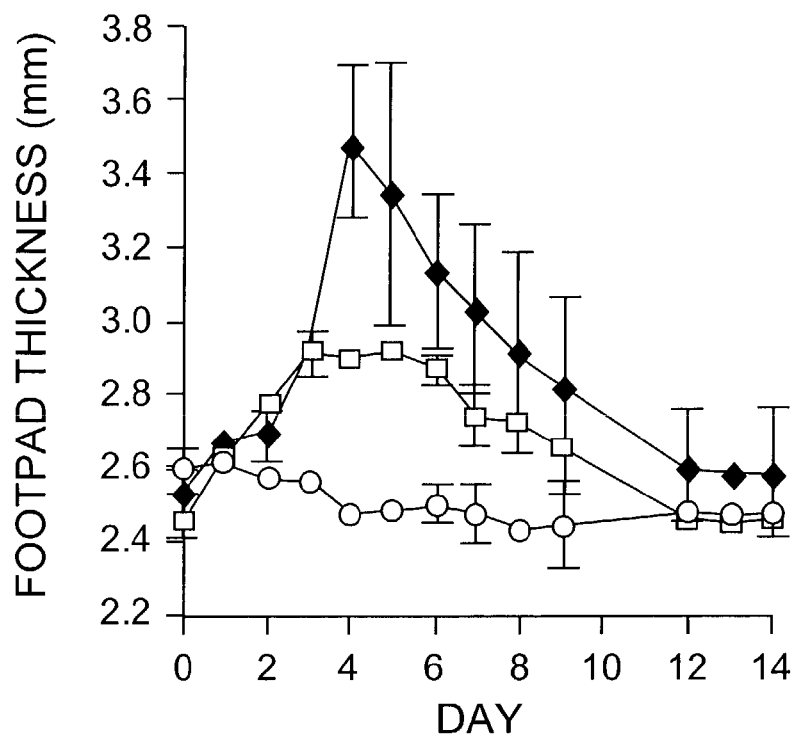
FIG. 1A shows footpad measurements of mice in three groups after hind footpad injections. The experimental group (open squares; n=4) had less footpad thickness after day 3 then the irrelevant monoclonal antibody group (filled diamonds; n=4). The no virus control group (open circles; n=4) maintained a consistent footpad thickness. The graph represents the results of one of three experiments.

While the virulence of orthopoxviruses naturally represents the cumulative effects of all of their proteins, SPICE appears to function as a potent inhibitor of human complement, thereby, creating a microenvironment around variola-infected cells so as to protect them from complement-mediated attack while they serve as a site for viral replication. Numerous attempts were made to generate antibodies to SPICE with little success. Therefore, to analyze the function of SPICE, monoclonal antibodies were raised against VCP to detect SPICE. Accordingly, one aspect of the present invention is a method of producing antibodies directed to SPICE by immunizing an animal with a complement regulatory protein and subsequently identifying antibodies, which specifically cross-react with SPICE. The complement regulatory protein may be isolated from any source including other Orthopoxviruses. In a preferred embodiment, the complement regulatory protein is VCP.

Antibodies may be generated using classical cloning and cell fusion techniques. In general, the antigen of interest is typically administered (e.g., intraperitoneal injection) to wild-type or inbred mice (e.g., BALB/c) or transgenic mice which produce desired antibodies, or rats, rabbits or other animal species which may produce native or human antibodies. The antigen may be administered alone, or mixed with adjuvant, or expressed from a vector (VEE replicon vector), or as DNA, or as a fusion protein to induce an immune response. Fusion proteins in the context of antibody production are defined as the peptide against which an immune response is desired coupled to carrier proteins, such as histidine tag (his), mouse IgG2a Fc domain, β-galactosidase, glutathione S-transferase, keyhole limpet hemocyanin (KLH), or bovine serum albumin, to name a few. In this manner, the peptides serve as haptens with the carrier proteins. After the animal is boosted, for example, two or more times, the spleen is removed and splenocytes are extracted and fused with myeloma cells using the well-known methodologies (e.g., see Kohler and Milstein (1975) *Nature* 256:495–497; Harlow and Lane, Antibodies: A Laboratory Manual, Cold Spring Harbor Laboratory, New York (1988)). The resulting hybrid cells are then cloned in a conventional manner, e.g., using limiting dilution, and the resulting clones, which produce the desired monoclonal antibodies, are cultured.

While monoclonal antibodies were used in the present invention, molecules or active fragments of molecules that bind to known antigens are also contemplated. Examples of active fragments of molecules that bind to known antigens include Fab, Fab', F(ab')$_2$, scFv, Fv, dsFv diabody, or Fd fragments. These active fragments may be derived from an antibody of the present invention by a number of techniques. For example, purified monoclonal antibodies may be cleaved with an enzyme, such as pepsin, and subjected to HPLC gel filtration. The appropriate fraction containing Fab fragments may then be collected and concentrated by membrane filtration and the like. For further description of general techniques for the isolation of active fragments of antibodies, see for example, Khaw et al. (1982) *J. Nucl. Med.* 23:1011–1019. The term "antibody" also includes humanized, bispecific and chimeric antibodies.

Antibodies which bind VCP or SPICE antigen are one aspect of the present invention. These monoclonal antibodies were raised against vaccinia VCP proteins; however, other orthopoxviruses are expected to contain VCP sequences at least 90% identical and which will likely produce antigens which elicit protective/neutralizing antibodies. An exemplary example of a homolog of VCP is SPICE. Other homologs of SPICE or VCP having at least 90% identity may be found in orthopoxviruses such as buffalopox virus, syn. vaccinia subspecies (buffalo, cattle, human); camelpox virus (camel); cowpox virus (rodents, felines, bovines, human); ectromelia virus (mousepox); monkeypox virus (rodents, primates, human); rabbitpox virus, syn. vaccinia subspecies (colonized rabbit); raccoonpox virus (North America raccoon); taterapox virus (African gerbil); and volepox virus (California pinon mouse and voles). Monocional antibodies against homologs from these orthopoxviruses provide protection against challenge with the source of immunogen virus.

Several antibodies raised against VCP antigen were also found to specifically cross-react with SPICE antigen. Binding of the antibodies of the present invention to VCP and SPICE was measured in an ELISA assay and by western blot analyses. However, other immunoassays that may be used to detect binding antibody-antigen interactions include, but are not limited to, radioimmunoassay, immunofluorescent assay, chemiluminescent assay, immunohistochemical assay and the like and may be performed in vitro, in vivo or in situ. Standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895–904. Three mAbs, 5A10, 5E7, and 1G1, recognized recombinant SPICE (rSPICE, SPICEFc or SPICEhis) over rVCP in competitive ELISA assays (Djavadi-Ohaniance and Friguet (1991) The specificity of monoclonal antibodies for enzymes in solution versus immobilized on solid phases (In: Immunochemistry of solid-phase immunoassay. J. Butler (ed.) CRC Press, Inc., Boca Raton, Fla., pp 203). Accordingly, in a preferred embodiment of the present invention, monoclonal antibodies raised against VCP which specifically cross-reacts with SPICE include 5A10, 5E7, or 1G1. It is contemplated that the reactivity of the antibodies is applicable against a broad variety of different wild-type and laboratory variola and vaccinia strains of different types.

It has now been found that passive administration of antibodies to VCP/SPICE disables viral complement regulatory proteins in orthopoxvirus infections. Anti-VCP/SPICE monoclonal antibodies or irrelevant monoclonal antibodies were passively administered to mice which had received intradermal footpad injections of vaccinia virus or phosphate buffered saline (PBS). Footpad thickness, as a measure of tissue swelling and inflammation, was recorded by day for each mouse and plasma samples were collected to evaluate for evidence of viremia. After day 3, footpad swelling in mice receiving anti-VCP monoclonal antibodies was diminished compared to footpad responses of mice receiving irrelevant monoclonal antibodies (FIG. 1A).

Figure 1B:
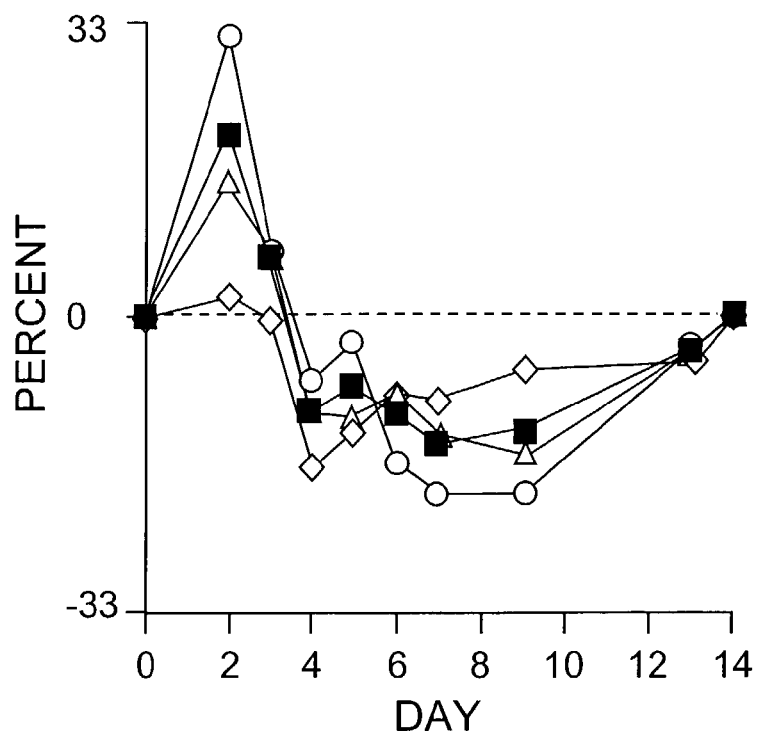
FIG. 1B shows the analysis of three experiments demonstrating percent deviation of mean footpad thickness of the experimental group from that of the irrelevant monoclonal antibody control group. Values were determined by calculating the difference between the experimental group and the irrelevant monoclonal antibody control group mean footpad thickness as a percentage of the irrelevant monoclonal antibody group mean footpad thickness for each day. Experiment I, shown in FIG. 1A (open diamonds, n=8); II (open triangles, n=12), and III (open circles, n=8), and a composite of the three experiments (filled squares) are plotted.

For days 1–3, the experimental group had greater footpad thickness (swelling) than the irrelevant monoclonal antibody control group ($p<0.0001$ for day 2 and $p=0.0262$ for day 3) (FIG. 1B). After day three, the overall difference between groups was highly significant ($p=0.0001$). The differences between groups ranged from 7.92% on day 5 ($p=0.03$), to 14.26% on day 7 ($p<0.0001$), to 3.96% on day 13 ($p=0.057$). These data indicate that the immune response of mice receiving anti-VCP antibodies started and resolved quicker than that of mice receiving irrelevant antibodies.

Using PCR methods of detecting viremia, as described herein, sequentially collected plasma samples as well as ovaries and kidneys at necropsy were analyzed by PCR for evidence of viremia and tissue spread. Viral DNA was below detectable levels in the tissues at necropsy, but viremia was apparent as early as day 2. Thus, intradermal injection of vaccinia may result in viremia. In one experiment, all six mice in the irrelevant monoclonal antibody control group had PCR evidence of viremia on day 4; however, two of six mice in the experimental group had evidence of viremia. Cumulative data for the three experiments involving 28 mice inoculated with vaccinia demonstrated that the experimental group and the irrelevant monoclonal antibody control group had approximately the same percentage of mice with viremia during days 1–3. However, after day 3, there was a precipitous decrease in the percentage of mice with viremia in the experimental group, while in the irrelevant monoclonal antibody group, 80% of mice had viremia, which persisted until day 6. The decreased percentage of mice with viremia in the experimental group reflected augmented viral clearance by complement-mediated lysis. Enhanced complement activity also resulted in neutralization of virus due to opsonization. Since the PCR assay detects viral DNA from both opsonized as well as non-opsonized viral particles, the actual percentage of mice with viremia may be lower.

These findings demonstrate that anti-VCP/SPICE antibodies decrease the frequency of viremia in a smallpox model of vaccinia infected mice by disabling viral complement regulatory proteins. Consequently, three complement-mediated processes occurred: viral particles were lysed and opsonized and virally infected cells were destroyed; C3a, C4a, and C5a triggered release of inflammatory mediators, which promoted inflammatory cell migration and edema; and endothelial cell activation by complement promoted coagulation, adhesion of leukocytes, formation of endothelial fenestrations and consequent edema (Volanakis (2002) *Curr. Top. Microbiol. Immunol.* 266:41). Hence, complement activity yielded rapid inflammation that contributed to swift viral clearance.

Accordingly, antibodies of the present invention are suitable both as therapeutic and prophylactic agents for treating or preventing vaccinia or variola infections. In general, this involves administering an effective amount of one or more antibodies of the present invention to a susceptible subject or one exhibiting variola or vaccinia infection. Any active form of the antibody may be administered, including Fab, Fab', $F(ab')_2$, scFv, Fv, dsFv diabody, or Fd fragments. Antibodies of the present invention may be produced in any system, including insect cells, baculovirus expression systems, chickens, rabbits, goats, cows, or plants such as tomato, potato, banana or strawberry. Methods for the production of antibodies in these systems are well-known to those skilled in the art of antibody production. Preferably, the antibodies used are compatible with the recipient species such that the immune response to the antibodies does not result in clearance of the antibodies before the virus is controlled, and the induced immune response to the antibodies in the subject does not induce "serum sickness" in the subject. Preferably, the antibodies administered exhibit some secondary functions such as binding to Fc receptors of the subject.

Treatment of individuals having variola or vaccinia infection involves the administration of an effective amount of one or more SPICE/VCP antibodies of the present invention. The antibodies may be provided in a kit and may be used or administered as a mixture, for example in equal amounts, or individually, provided in sequence, or administered all at once. In providing a patient with antibodies, or fragments thereof, which bind to SPICE or VCP antigen, or an antibody which protects against variola or vaccinia virus in a recipient patient, the dosage of administered agent will vary depending upon such factors as the patient's age, weight, height, sex, general medical condition, previous medical history, etc. Specific doses may be determined by the skilled clinician upon consideration of these factors.

Antibodies for protecting against variola or vaccinia virus are intended to be provided to recipient subjects in an amount sufficient to effect a reduction in the variola or vaccinia virus infection symptoms. When administering an antibody which protects against variola or vaccinia virus, preference is given to antibody 1G1. 1G1 has been shown to bind to and inhibit the function of VCP and SPICE and attenuate vaccinia infection. In contrast, antibody 5A10 binds to VCP and SPICE but does not inhibit the activity of VCP or SPICE and is less effective at attenuating vaccinia virus infections. An amount is said to be sufficient to "effect" the reduction of infection symptoms if the dosage, route of administration, etc. of the agent are sufficient to influence such a response. Responses to antibody administration may be measured by, for example, analysis of subject's vital signs, skin lesions, levels of viremia, and the like.

The present invention still further pertains to a method of administering an effective amount of one or more antibodies against SPICE or VCP in conjunction with vaccinia virus vaccine to modulate side effects associated with said vaccine. Side effects associated with vaccinia virus vaccine include tissue destruction, relentless progressive pock lesions, encephalitis, and metastatic viral lesions far from the site of inoculation. Healthy vaccines have developed accidental vaccinia infection by autoinoculation to other body sites, such as the eye; ocular vaccinia may lead to blindness. Immunosuppressed vaccinees, which include pregnant women and individuals with eczema, cancer, or other immunodeficiencies, often have more severe side effects. These severe side effects include fetal vaccinia, eczema vaccinatum, vaccinia necrosum, progressive vaccinia or vaccinia gangrenosum. In a preferred embodiment, administration of SPICE or VCP antibodies for protecting against vaccinia virus side effects are intended to be provided to recipient subjects in an amount sufficient to effect a reduction in the vaccinia virus vaccine symptoms.

Another therapeutic use of the antibodies of the present invention is active immunization of a patient using an anti-idiotypic antibody raised against a monoclonal antibody of the present invention. Immunization with an anti-idiotype, which mimics the structure of the epitope, elicits an active anti-SPICE or anti-VCP response (Linthicum, D. S. and Farid, N. R., Anti-Idiotypes, Receptors, and Molecular Mimicry (1988), pp 1–5 and 285–300).

Likewise, active immunization may be induced by administering one or more antigenic and/or immunogenic epitopes of SPICE or VCP as a component of a subunit vaccine. VCP binding sites of each antibody were determined by flow cytometry using mouse fibroblast lines expressing 2, 3 or 4 contiguous VCP short consensus repeats (SCRs) as cell surface receptors. By determining to which cell lines a mAb bound and to which cell line it did not bind, the SCR binding site of the mAb was determined. For example, mAb 5A10 recognized the three cell lines expressing SCR1 of VCP, but did not recognize the three cell lines that expressed a VCP mutant lacking SCR1. Therefore, it was concluded that mAb 5A10 recognized an epitope on SCR1. The term epitope as used herein, is generally understood by those of skill in the art to refer to the region of an antigen, such as SCR1 for example, that specifically interacts with an antibody. An epitope of a peptide or protein antigen may be formed by contiguous or noncontiguous amino acid sequences of the antigen. VCP and SPICE, like many proteins, contains many epitopes. The epitopes or peptides recognized by the antibodies of the present invention and conservative substitutions of these peptides which are still recognized by the antibody are an embodiment of the present invention. These peptides offer a convenient method for eluting the variola or vaccinia antigen bound to the respective antibody on immunoaffinity columns. For example, when an antibody which recognizes an epitope for SPICE is used in an immunoaffinity column to purify SPICE, the peptide recognized by the antibody may be added to the immunoaffinity column to elute SPICE. Further, truncation of these epitopes may be possible since antigenic epitopes have been reported to be represented by as few as five amino acid residues. In a preferred embodiment of the present invention, monoclonal antibodies binding to SCR1 of a viral complement regulatory protein include 5A10 or 6E5. In another preferred embodiment, monoclonal antibodies binding to SCR2 of a viral complement regulatory protein include 3D9 or 6C4. In yet another preferred embodiment, monoclonal antibodies binding to SCR3 of a viral complement regulatory protein include 2F10 or 5E7. In yet another preferred embodiment, monoclonal antibodies binding to SCR4 of a viral complement regulatory protein include 1G1, 5A1 or 5E1.

By further mapping binding sites of the monoclonal antibodies described herein, other peptides useful as a vaccine or a therapeutic may be identified. Therefore, the invention further relates to a method for identifying protective antigenic epitopes comprising (i) reacting a monoclonal antibody to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides may then be assayed for their ability to protect an animal from disease, or to reduce the severity of disease.

The epitopes or peptides on the SPICE antigen to which the antibodies bind may constitute all or part of an active vaccine candidate. An active vaccine or therapeutic candidate may include these peptide sequences and others. The epitopes or peptides may be delivered as synthetic peptides, or as fusion proteins, alone or co-administered with cytokines and/or adjuvants or carriers safe for human use, e.g., aluminum hydroxide, to increase immunogenicity. In addition, sequences such as ubiquitin may be added to increase antigen processing for more effective immune responses. In a preferred embodiment, SPICE or VCP or epitopes or peptides of the SPICE or VCP are fused to one, two or three or more copies of C3d (see, e.g., Dempsey, et al. (1996) *Science* 271:348–50). These fusion proteins result in 100- and 10,000-fold more immunogenic peptides by binding to complement receptor 2 (CR2; CD21).

Vaccination may be performed orally or parenterally in amounts sufficient to enable the recipient to generate protective antibodies against biologically functional regions of SPICE or VCP, prophylactically or therapeutically. The host may be actively immunized with the antigenic/immunogenic peptide in pure form, a fragment of the peptide, or a modified form of the peptide. One or more amino acids, not corresponding to the original protein sequence may be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used, e.g., $NH_2$-acetylation or COOH-terminal amidation, to provide additional means for coupling or fusing the peptide to another protein or peptide molecule or to a support.

An active vaccine or therapeutic candidate may also be in the form of a DNA vaccine. An alternative to a traditional vaccine comprising an antigen and an adjuvant, is directed to in vivo introduction of DNA encoding the antigen into tissues of a subject for expression of the antigen by the cells of the subject's tissue. Such vaccines are termed herein "DNA vaccines" or "nucleic acid-based vaccines." DNA vaccines are described in WO 95/20660 and WO 93/19183, the disclosures of which are hereby incorporated by reference in their entireties. Direct injection of DNA encoding a viral protein to elicit a protective immune response has been demonstrated in numerous experimental systems (Conry, et al. (1994) *Cancer Res.* 54:1164–1168; Cox, et al. (1993) *Virology* 67:5664–5667; Davis, et al. (1993) *Hum. Mole. Genet.* 2:1847–1851; Sedegah, et al. (1994) *Proc. Natl. Acad. Sci. USA* 91:9866–9870; Montgomery, et al., (1993) *DNA Cell Bio.* 12:777–783; Ulmer, et al., (1993) *Science* 259:1745–1749; Wang, et al. (1993) *Proc. Natl. Acad. Sci. USA* 90:4156–4160; Xiang, et al. (1994) *Virology* 199: 132–140). Neutralization of influenza virus has been used for both envelope and internal viral proteins to induce the production of antibodies, but in particular have focused on the viral hemagglutinin protein (HA) (Fynan, et al. (1993) *DNA Cell. Biol.* 12:785–789; Fynan, et al. (1993) *Proc. Natl. Acad. Sci. USA* 90:11478–11482; Robinson, et al. (1993) *Vaccine* 11:957; Webster, et al. (1994) *Vaccine* 12:1495–1498). A DNA vaccine encoding a C3d fusion of HA from influenza virus, has been developed (Ross, et al. (2000) *Nat. Immunol.* 1(2):127–31). Analysis of the titers, avidity maturation, and hemagglutinin-inhibition activity of raised antibody revealed that immunizations with the HA-3C3d DNA accelerated both the avidity maturation of antibody to HA and the appearance of hemagglutinin-inhibition activity. These accelerated antibody responses correlated to a more rapid appearance of protective immunity. They also correlated to complete protection from live virus challenge by a single vaccination at a dose ten times lower than the protective dose for non-C3d forms of HA.

Vaccination through directly introducing nucleic acid sequences that encode a SPICE or VCP protein or fusion protein of SPICE or VCP to elicit a protective immune response produces both cell-mediated and humoral responses. This is analogous to results obtained with live viruses (Raz, et al. (1994) *Proc. Natl. Acad. Sci. USA* 91:9519–9523; Ulmer (1993) supra; Wang (1993) supra; Xiang (1994) supra). Studies with ferrets indicate that DNA vaccines against conserved internal viral proteins of influenza, together with surface glycoproteins, are more effective against antigenic variants of influenza virus than are either inactivated or subvirion vaccines (Donnelly, et al. (1995) *Nat. Medicine* 6:583–587). Indeed, reproducible immune responses to DNA encoding nucleoprotein that last essentially for the lifetime of the animal have been reported in mice (Yankauckas, et al. (1993) *DNA Cell Biol.* 12:771–776). Accordingly, another aspect of the present invention provides a DNA vaccine containing nucleic acid sequences encoding SPICE or VCP or antigenic epitopes thereof. In a more preferred embodiment, a DNA vaccine includes DNA encoding SPICE or VCP fused to one, two or three or more copies of C3d.

Another aspect of the present invention relates to the administration of VCP or SPICE or derivatives or fusion proteins thereof or DNA vaccines containing nucleic acid sequences encoding SPICE or VCP or antigenic epitopes thereof prior to the administration of vaccinia virus vaccine to attenuate the virulence of the vaccinia virus. The preimmunization step would be beneficial to immunocompromised individuals or individuals who may suffer from the side effects associated with the vaccinia virus vaccine.

The compounds of the present invention may be formulated according to known methods to prepare pharmaceutically useful compositions, whereby these materials, or their functional derivatives, are combined in admixture with an acceptable carrier. Suitable carriers and their formulation, inclusive of other human proteins, e.g., human serum albumin, are described, for example, in Remington: The Science and Practice of Pharmacy, Alfonso R. Gennaro, editor, 20th ed. Lippincott Williams & Wilkins: Philadelphia, Pa., 2000. In order to form an acceptable composition suitable for effective administration, such compositions may contain an effective amount of the above-described compounds together with a suitable amount of carrier.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethyl-cellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules, for example, hydroxymethylcellulose, gelatin-microcapsules, or poly (methylmethacylate)-microcapsules, or in colloidal drug delivery systems, for example, liposomes, albumin microspheres, microemulsions, nanoparticles, and nanocapsules or in macroemulsions. Such techniques are disclosed in Remington (2000) supra. Furthermore, additional pharmaceutical methods may be employed to incorporate the compositions of the present invention into as a lining of surgical tubing.

Administration of a pharmaceutical composition disclosed herein may be carried out by any suitable means, including parenteral injection (such as intraperitoneal, subcutaneous, or intramuscular injection), orally, or by topical application to an airway surface. Topical application to an airway surface may be carried out by intranasal administration (e.g., by use of dropper, swab, or inhaler which deposits a pharmaceutical formulation intranasally). Topical application to an airway surface may also be carried out by inhalation administration, such as by creating respirable particles of a pharmaceutical formulation (including both solid particles and liquid particles) containing the active ingredient as an aerosol suspension, and then causing the subject to inhale the respirable particles. Methods and apparatus for administering respirable particles of pharmaceutical formulations are well known, and any conventional technique may be employed. Oral administration may be in the form of an ingestible liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention still further pertains to methods for detecting SPICE or VCP in a sample suspected of containing variola or vaccinia. One method includes contacting the sample with an antibody which specifically binds an epitope of SPICE or VCP antigen, allowing the antibody to bind to the SPICE or VCP antigen to form an antibody-antigen complex, washing the sample, detecting the formation of the antibody-antigen complex and correlating the presence or absence of the antibody-antigen complex with the presence or absence of SPICE or VCP antigen in the sample. A sample is intended to include biological material, e.g., cells, tissues, or biological fluid as well as environmental materials, e.g., soil and water, and food samples including canned goods, meats, and others. Antibodies specific to SPICE or VCP antigen which may be useful in this detection method are provided herein. It is contemplated that more than one antibody may be used to differentiate between the presence of SPICE or VCP. For example, an antibody specific to VCP (e.g., monoclonal antibody 5A10, 6E5, 3D9, 6C4, 2F10, 5E7, 1G1, 5A1, or 5E1) may be used in conjunction with an antibody which binds both VCP and SPICE (e.g., monoclonal antibody 5A10, 5E7, or 1G1). The formation of an antibody-antigen complex in the presence of either antibody is indicative of the presence of VCP, whereas the formation of an antibody-antigen complex in the presence of an antibody which binds both VCP and SPICE, but not in the presence of an antibody specific to VCP, is indicative of the presence of SPICE.

The detection of the formation of the antibody-antigen complex is intended to include detection of the presence or absence of SPICE or VCP antigen in a sample. The presence or absence of SPICE or VCP antigen may be detected using an immunoassay. A number of immunoassays used to detect and/or quantitate antigens are well known to those of ordinary skill in the art. See, e.g., Harlow and Lane, Antibodies: A Laboratory Manual, Cold Spring Harbor Laboratory, New York (1988) 555–612. Such immunoassays are well-known in the art and include antibody capture assays, antigen capture assays, and two-antibody sandwich assays. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a vaccinia virus vaccinee and an antibody of the present invention are allowed to compete for binding of the antigen. The amount of antibody bound is then measured and a determination is made as to whether the serum contains SPICE antibodies. This competitive ELISA may be used to indicate immunity to known protective epitopes following vaccination or following treatment with SPICE-3C3d DNA vaccine.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that may bind to the antigen.

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Antibodies useful in these assays include monoclonal antibodies, polyclonal antibodies, or affinity purified polyclonal antibodies. Those of ordinary skill in the art know other suitable labels which may be employed in accordance with the present invention. The binding of these labels to antibodies or fragments thereof may be accomplished using standard techniques commonly known to those of ordinary skill in the art. Typical techniques are described by Kennedy, et al. ((1976) *Clin. Chim. Acta* 70:1–31), and Schurs, et al. ((1977) *Clin. Chim Acta* 81:1–40). Coupling techniques mentioned in the latter are the glutaraldehyde method, the periodate method, the dimaleimide method, and others.

Yet another aspect of the present invention is a kit for detecting the presence of SPICE or VCP in a sample. The kit includes a container holding one or more antibodies which bind an epitope of SPICE or VCP antigen and instructions for using the antibody for the purpose of binding to SPICE or VCP antigen to form an antibody-antigen complex and detecting the formation of the antibody-antigen complex such that the presence or absence of the antibody-antigen complex correlates with presence or absence of variola or vaccinia virus in the sample. Examples of containers include multiwell plates which allow simultaneous detection of variola or vaccinia virus in multiple samples.

An alternative method of detecting SPICE or VCP pertains to the detection of nucleic acid sequences encoding SPICE or VCP. In one preferred embodiment, RFLP variations present within VCP and SPICE genes are differentiated using the restriction endonuclease SspI. This recognition site is present in the SPICE genes of various variola strains, e.g., Variola virus strains Garcia—1966, Congo —1965, and Somalia—1977, and *Variola Major* virus strains India—1967 and Bangladesh—1975, due to the leucine to serine difference in SCR4 of variola versus vaccinia virus. However, the recognition site is absent in the VCP gene of vaccinia virus strains such as WR and Copenhagen and also absent in the complement regulatory protein (also known as Inflammatory Modulating Protein) of cowpox virus strain Grishak. The present invention uses this unique restriction site in the SCR4 region of SPICE to specifically detect the presence of variola virus in a sample.

Accordingly, a method of detecting, in a sample, nucleic acid sequences encoding SPICE or VCP, involves subjecting DNA isolated from a subject to a Polymerase Chain Reaction (PCR), wherein the PCR employs at least two oligonucleotide primers that anneal to the nucleic acid sequences encoding SPICE or VCP. One of the primers is complementary to a first nucleotide sequence 5' of a diagnostic SspI site unique to the SCR4 region of variola virus SPICE or the homologous region of vaccinia virus VCP. Such a primer is preferably 50, 100, or 200 bp 5' of the SspI site and most preferably corresponds to SEQ ID NO:11 or SEQ ID NO:13. The second primer is complementary to a second nucleotide sequence 3' of a diagnostic SspI site unique to the SCR4 region of variola virus SPICE or the homologous region of vaccinia virus VCP. Such a primer is preferably 50, 100, or 200 bp 3' of the SspI site and most preferably corresponds to SEQ ID NO:12. In accordance with this method, a geometrically amplified product is obtained only when the first and second nucleotide sequences occur within the same nucleic acid molecule encoding SPICE or VCP. The fundamentals of PCR are well-known to the skilled artisan, see, e.g., McPherson, et al., PCR, A Practical Approach, IRL Press, Oxford, Eng. (1991). A subsequent step for the specific detection of SPICE DNA is to endonuclease digest the resulting PCR amplicon with SspI. Digestion of amplified fragments with SspI results in the detection of two fragments for the SPICE gene (e.g., approximately 576 and 157 bp when using primers of SEQ ID NO:11 and SEQ ID NO:12 or approximately 166 bp and 266 bp when using primers of SEQ ID NO:12 and SEQ ID NO:13) and only one fragment for the VCP or IMP gene (e.g., approximately 730 bp when using primers of SEQ ID NO:11 and SEQ ID NO:12 or approximately 432 bp when using primers of SEQ ID NO:12 and SEQ ID NO:13). Using primer pairs of consensus sequences encoding SPICE or VCP (SEQ ID NO:13 and SEQ ID NO:12), it was found that as few as $10^3$ pfu of vaccinia virus in 100 µl of plasma could be detected.

The present invention also provides kits which are useful for carrying out the nucleic acid detection methods of the present invention. A kit of the invention contains primers of SEQ ID NO:11 and/or SEQ ID NO:13 in combination with a primer of SEQ ID NO:12 to amplify SPICE or VCP. The kit may further contain the restriction enzyme SspI to differentiate between SPICE and VCP present in a sample. The kit may also contain other solutions necessary or convenient for carrying out the invention (e.g., PCR buffers, a polymerase, and a restriction enzyme). The container may be made of glass, plastic or foil and may be a vial, bottle, pouch, tube, bag, etc. The kit may further contain written information, such as procedures for carrying out the present invention or analytical information, such as the amount of reagent contained in the first container. The container may be in another container, e.g., a box or a bag, along with the written information.

A further aspect of the present invention involves fusion proteins of SPICE and VCP. Recombinant protein "rSPICE", as used herein includes, but is not limited to, histidine-tagged SPICE (SPICEhis) or mouse IgG2a Fc-tagged SPICE (SPICEFc). Likewise recombinant protein "rVCP", as used herein includes, but is not limited to, histidine-tagged VCP (VCPhis) or mouse IgG2a Fc-tagged VCP (VCPFc).

SPICE was generated by mutating VCP amino acid sequence into that of SPICE. To facilitate purification of SPICE and VCP polypeptide, his and Fc tags were fused to the polypeptides. Analysis of the fusion polypeptides revealed that SPICEhis, VCPhis, SPICEFc, and VCPFc migrated as single bands under reducing conditions on 12% sodium dodecyl sulfate-polyacrylamide gel electrophoresis (SDS-PAGE) at 33, 35, 53, and 55 kDa, respectively. The Fc-fusion polypeptides migrated at approximately 110 kDa under non-reducing conditions, representing dimers of VCP or SPICE due to disulfide bonds between two Fc domains (De Preval et al. (1970) Nature 228:930–932). The recombinant proteins produced in mammalian and insect cells migrated on SDS-PAGE and functioned identically.

The molecular mass of SPICEhis and VCPhis by mass spectrometry was 28,943 and 29,057 Da, respectively; very close to the predicted molecular masses of 28,936 and 28,818 Da, but different from the molecular mass observed on SDS-PACE. To investigate the discrepancy between the molecular mass established by mass spectrometry versus SDS-PAGE, wild-type VCP, secreted into the media of vaccinia-infected cells, was identified by western blot and shown to co-migrate with VCPhis at approximately 35 kDa, consistent with previously published mass of wild-type VCP (Kotwal, et al. (1990) supra). Moreover, glycosylation experiments were negative and mass spectrometry analysis detected no evidence of glycosylation or acylation. Therefore, the discrepancy in the apparent molecular mass of viral complement regulatory proteins on SDS-PAGE with the determined value by mass spectrometry may be artifactual.

The molecular engineering and expression of SPICE confirmed that variola produces a compact, functionally active cofactor for factor I. C3b degradation experiments were performed to compare the cofactor activity of SPICE, VCP, soluble human CR1 (sCR1; Weisman, et al. (1990) Science 249:146–151), and H factor at normal ionic strength. Soluble CR1 is a recombinant, soluble protein consisting of 30 SCRs of CR1, but lacking the transmembrane and cytoplasmic domains (Weisman, et al. (1990) supra). Soluble CR1 is the most potent inhibitor of complement activation known, however, it is eight times larger in size than SPICE. The C3bα' cleavage fragments migrate as follows: 68 kDa, 46 kDa (iC3b$_1$), 43 kDa (iC3b$_2$), and <35 kDa (C3dg/C3c). C4bα' cleavage fragments migrate as follows: 64 kDa (iC4b), 46 kDa (C4d), and 25 kDa (C4c).

The cofactor activity of SPICE was robust, with C3b cleavage to iC3b$_2$ occurring almost immediately, followed by cleavage to C3c/C3dg (sampled at 0, 4 and 24 hours). In the presence of VCP, C3b was degraded more slowly, first to iC3b$_1$ and then to iC3b$_2$. However, VCP did not participate in further degradation of iC3b$_2$ to C3c/C3dg, even after 24 hours. Therefore, qualitatively, SPICE functions more like factor H, which serves as a cofactor for factor I in the degradation of iC3b$_2$ to C3c/C3dg after longer incubations (Ross, et al. (1982) J. Immunol. 129:2051–2060). Although not as potent as sCR1, SPICE may result in a similar degradation pattern where C3dg is formed (Weisman, et al. (1990) supra). Identical experiments were performed for C4b. At 0.65 µM, SPICEhis and VCPhis as cofactors appear to function identically and result in the degradation of C4b to C4c/C4d. Factor H also works as a cofactor for factor I degradation of C4b in the fluid phase (Pangburn, et al. (1977) J. Exp. Med. 146:257–270).

Using 100-fold lower concentrations (0.68 µM) of recombinant cofactors, differences in efficiency were established. In the presence of SPICEhis, 50% of the C3α' chain was degraded in less than 5 minutes, and entirely degraded by 15 minutes, as compared to nearly complete degradation of the C3α' chain in 7 minutes by sCR1. However, only 25% of the C3bα' chain was degraded after 120 minutes with VCP. Therefore, SPICEhis functions as a cofactor for factor I in the degradation of C3b with at least 100-fold greater efficiency than VCPhis. Soluble CR1 functions at least twice as fast as SPICEhis possibly due to the three ligand binding sites of CR1 (Klickstein, et al. (1988) J. Exp. Med. 168: 1699–711; Krych, et al. (1991) Proc. Natl. Acad. Sci. USA 88:4353–7; Kalli, et al. (1991) J. Exp. Med. 174:1451–60; Krych, et al. (1994) J. Biol. Chem. 269:13273–8). Furthermore, at this low concentration of SPICE and VCP, the degradation patterns showed that with SPICEhis, the C3bα' chain was immediately cleaved to iC3b$_1$, followed by cleavage to iC3b$_2$, while with VCPhis, no such degradation to iC3b$_2$ was observed, consistent with Sahu, et al. ((1998) J. Immunol. 160:5596–5604). Unlike cobra venom factor and Compstatin, a 13-residue cyclic peptide complement inhibitor, which inhibit cleavage of C3, SPICE inhibits the active form of C3, i.e., C3b.

Similarly, kinetic experiments using C4b were performed. At limiting concentration of recombinant proteins (0.68 µM), 50% of the C4bα' chain was degraded in 15 minutes with sCR1, 20 minutes with SPICEhis, and 120 minutes with VCPhis. At this concentration, therefore, SPICEhis functions approximately 6-fold faster than VCPhis, but slower than sCR1. Minimal improvement in SPICEhis and VCPhis cofactor activity with both ligands (C3b and C4b)

was observed at half-ionic strength solution. Accordingly, a preferred embodiment of the present invention provides a fusion protein comprising SPICE and a tag comprising his or Fc that binds human complement components C4b, C3b, iC3b$_1$, iC3b$_2$, or iC4b. In a preferred embodiment, the SPICE fusion protein binds complement components C3b or C4b.

It has now been found that monoclonal antibodies binding to SPICE or VCP are useful in inhibiting the degradation of C3b or C4b by SPICE or VCP. Results indicated that both 1G1 and 5E7 inhibited the degradation of C3b and C4b by SPICE, while mAbs 6E5 (anti-SCR1), 3D9 (anti-SCR2), 6C4 (anti-SCR2), and 1G1 (anti-SCR4) inhibited the function of VCP in the degradation of both ligands. In addition, 5E1 (anti-SCR4) inhibited VCP in the degradation of C3b only. These data indicate that SCR4 is critical for VCP and SPICE cofactor activity, SCR1 and SCR2 are critical for VCP, and SCR3 is necessary for SPICE cofactor activity. It is contemplated that additional SCRs may be important in the cofactor function of SPICE or VCP as only three and nine antibodies were evaluated for SPICE and VCP, respectively.

Since mammalian CRPs exhibit homologous restriction, that is, they function best against complement from phylogenetically related species (Dalmasso, A. P. Role of Complement in Graft Rejection. In The Complement System, Vol. 1 (eds. Rother, K., Till, G. O., & Hansch, G. M.) 471–486 (Springer-Verlag, Berlin, 1997)), it was determined whether variola exhibits "host complement restriction", particularly due to its restricted host range. Therefore, the ability of rSPICE and rVCP to inhibit complement from human, baboon, dog, guinea pig was tested in hemolytic assays.

From these experiments it was shown that both complement pathways were inhibited by rSPICE and rVCP. However, relative to VCPFc, SPICEFc preferentially inhibited human and baboon complement versus dog and guinea pig complement. Similarly, relative to SPICEhis, VCPhis preferentially inhibited dog and guinea pig complement versus human and baboon complement. In these experiments, however, Fc constructs behaved less efficiently than the his-tagged constructs possibly as a result of the Fc constructs forming dimers between the Fc domains; the cofactor's function may be more potent in the monomeric, his-tagged form. Since the specific interaction between cofactor proteins, ligands, and factor I have not been clearly defined, it is not clear the role that a dimeric form might have on the interaction of these components. Fc fusions are preferred because they last longer in the blood, therefore, Fc constructs may be modified to block disulfide bond formation which lead to Fc dimers. Nonetheless, the hemolysis studies indicate that the complement preference of SPICE parallels the host preference of the virus. Accordingly, a preferred embodiment of the present invention is a fusion protein comprising a tag fused to SPICE.

In a further aspect, the invention provides a method for modulating a complement-mediated disorder in a mammal, i.e., any condition in which complement activity is undesirably high. Examples of complement-mediated disorders include, but are not limited to, inflammation (including neurological inflammation), spinal cord injuries, arthritis, ischemia-induced reperfusion injuries, glomerulonephritis, encephalomyelitis, and burns. Also, to be considered are situations where complement activation leads to increased morbidity, such as occurs when serum, plasma or blood is perfused through tubing or plastics as in cardiopulmonary bypass, dialysis and the like. An inhibition effective amount of rSPICE or rVCP is an amount that inhibits at least 20%, preferably 50%, and most preferably 90% of undesired complement activity. If desired, an effective amount of rSPICE or rVCP that inhibits a complement-mediated disorder may be identified as an amount that ameliorates a sign(s) or symptom(s) of a complement-mediated disorder. The examples, which follow, are set forth to illustrate the present invention, and are not to be construed as limiting thereof.

EXAMPLE 1

Molecular Engineering, Expression and Purification of Recombinant SPICE

SPICE was generated by mutating the VCP amino acid sequence into that of SPICE. Thirteen nucleotide mutations, generated using standard methods, resulted in 11 amino acid substitutions (Table 1). Twenty-two primers (Life Technologies, Inc, (LTI) Grand Island, N.Y.) were designed with the following point mutations: T was substituted for A at position 339 of the VCP DNA sequence (Kotwal and Moss (1988) *Nature* 335:176–178), T for C400, A for C416, A for G430, A for G466, T for C500, AAT for GAG 538–540, A for G640, T for C686, C for A749, and C for A814. The DNA sequence was confirmed by 377 Stretch sequencer (Applied Biosystems Inc., Foster City, Calif.). To facilitate purification of recombinant SPICE (rSPICE) and VCP (rVCP) proteins, two constructs for each protein were designed. One construct encoded for six histidines at the carboxy-terminus (his-tag or his), while the other encoded for a carboxy-terminus mouse IgG2a Fc domain (Fc). SPICE was substituted for VCP in three plasmids (pRelVCP1234, pApHygVCPFc, and pVCPFc; Rosengard et al. (1999) *Mol. Immunol.* 36:685–697)) previously used to express VCPFc in 293T cells. Recombinant baculoviruses were created by subcloning SPICEFc and VCPFc EcoRI/XbaI fragments into pFASTBAC™HTa (BAC-TO-BAC® system, LTI) to create pFastBacHTaSPICEFc and pFasLBacHTaVCPFc and novel recombinant baculovirus strains containing SPICEFc and VCPFc.

TABLE 1

| Location | Amino Acid Sequence |
|---|---|
| SCR1: | |
| SPICE | CCTIPSRPINMKFKNSVETDANANYNIGDTIEYLCLPGYRKQKMGPIYAKCTGTGWTLFNQCIKRR (SEQ ID NO:1) |
| VCP | CCTIPSRPINMKFKNSVETDANANYNIGDTIEYLCLPGYRKQKMGPIYAKCTGTGWTLFNQCIKRR (SEQ ID NO:2) |
| SCR2: | |

TABLE 1-continued

| Location | Amino Acid Sequence |
|---|---|
| SPICE | CPSPRDIDNGHLDIGGVDFGSSITYSCNSGYYLIGEYKSYCKLGSTGSMVWNPKAPICESVK (SEQ ID NO:3) |
| VCP | CPSPRDIDNGQLDIGGVDFGSSITYSCNSGYHLIGESKSYCELGSTGSMVWNPEAPICESVK (SEQ ID NO:4) |
| SCR3: | |
| SPICE | CQLPPSISNGRHNGYNDFYTDGSWTYSCNSGYSLIGNSGVLCSGGEWSNPPTCQIVK (SEQ ID NO:5) |
| VCP | CQSPPSISNGRHNGYEDFYTDGSWTYSCNSGYSLIGNSGVLCSGGEWSDPPTCQIVK (SEQ ID NO:6) |
| SCR4: | |
| SPICE | CPHPTILNGYLSSGFKRSYSYNDNVDFTCKYGYKLSGSSSSTCSPGNTWQPELPKCVR (SEQ ID NO:7) |
| VCP | CPHPTISNGYLSSGFKRSYSYNDNVDFKCKYGYKLSGSSSSTCSPGNTWKPELPKCVR (SEQ ID NO:8) |

Underlined residues indicate amino acid substitutions.

A baculovirus construct containing a placental alkaline phosphatase leader sequence (Mroczkowski et al (1994) *J. Biol. Chem.* 269:13522–13528) and six histidines at the carboxy-terminus was created using a PCR-based approach. Oligonucleotides 99AMR1 (5'-GCA CCC GGG AGT TCT ATC ATG CTG TAC TAT TCC G-3'; SEQ ID NO:9) and HISSTOP (5'-GCT CTA GAC TCG AGC TAG TGG TGG TGG TGG TGG TGG CGT ACA CAT TTT GGA AGT TC-3'; SEQ ID NO:10) were used. The novel SPICE and VCP PspAI/XhoI fragments were ligated into pBLUE-SCRIPT® II KS phagemid (Stratagene, La Jolla, Calif.) and subsequently subcloned into pFastBac™ at XbaI/XhoI sites to generate pFBSPICEhis and pFBVCPhis. Concurrently, the alkaline phosphatase leader from pPbac (Stratagene) was cleaved using NheI/PspAI and ligated to generate pFBap-SPICEhis and pFBapVCPhis, which were used to generate baculovirus containing SPICEhis and VCPhis.

Recombinant proteins were produced either in 293T cells (Rosengard et al. (1999) *Mol. Immunol.* 36:685–697) or in *Spodoptera frugiperda* (Sf9 cells; LTI) and affinity purified from culture supernatant using CL-4B protein A beads (Amersham Pharmacia, Uppsala, Sweden) or Ni-NTA Superflow (Qiagen, Valencia, Calif.). Recombinant proteins were dialyzed against phosphate buffered saline (PBS; LTI). Characterization of SPICEhis and VCPhis by mass spectrometry was performed (M-Scan, West Chester, Pa.).

EXAMPLE 2

Anti-VCP and Anti-SPICE Monoclonal Antibodies

Generation of anti-SPICE/VCP monoclonal antibodies (mAb). Production to anti-SPICE/VCP mAbs was performed using standard methods. Briefly, 4–6 week old BALB/c mice (The Jackson Lab, Bar Harbor, Me.) were immunized intraperitoneally with ~35 μg of recombinant VCP (rVCP, either VCPFc or VCPhis) in complete Freund's adjuvant (FA) and later boosted with ~35 μg of protein in incomplete FA. Splenic cells ($1\times10^8$) were fused with myeloma cells ($1\times10^8$; SP2/0-Ag 14 cells; ATCC #CRL 1581, Manassas, Va.). Master clones were twice subcloned and subsequently injected intraperitoneally into pristane-treated BALB/c mice. MAbs were purified from ascites fluid using Protein G Sepharose slurry (Amersham Pharmacia, Uppsala, Sweden).

Identification of wild-type VCP using polyclonal anti-SPICE/VCP antibodies. Anti-VCP mAb identified wild-type VCP in serum-free media (DMEM; Life Technologies, Inc., Rockville, Md.) from four 75 $cm_2$ flasks of BS-C-1 cells (CCL-26, ATCC) previously infected with 10 plaque forming units/cell of vaccinia virus strain Western Reserve (WR). Medium was concentrated 1000-fold, fractionated by SDS-PAGE, and transferred to nitrocellulose membrane. Western blot analysis was performed using polyclonal anti-VCP antiserum (1:1000 dilution), followed by biotin-conjugated goat anti-mouse IgG (1:100,000 dilution; Sigma, St. Louis, Mo.), avidin-peroxidase (1:10,000), and TMB Membrane Peroxidase Substrate System Kit (Kirkegaard and Perry Laboratories, Inc. (KPL), Gaithersburg, Md.).

Mapping of anti-SPICE/VCP mAb to short consensus repeats of VCP. Nine mAb were generated from mice injected with rVCP. The binding site on VCP of each mAb was determined by flow cytometry using previously described mouse fibroblast cell lines (L-M(TK), CCL1.3; ATCC) that express 2, 3, or 4 contiguous VCP short consensus repeats as cell surface receptors (Rosengard et al. (1999) *Mol. Immunol.* 36:685–697). VCP and VCP deletion mutants were rendered membrane bound by replacing SCRs 1 and 2 of complement receptor 2 (CR2; CD21; Lowell, et al. (1989) *J. Exp. Med.* 170:1931) with VCP or a VCP deletion mutant. The cells stably express SCR1-2,2-3, 3-4, 1-3, 2-4, or 1-4 of VCP. These fibroblasts and wild-type L-cells were incubated with each monoclonal antibody, followed by fluorescein-conjugated F(ab')$_2$ goat anti-mouse IgG (50 μL; Jackson Immunoresearch, West Grove, Pa.) and analyzed on a flow cytometer (FACScan; Becton-Dickinson, San Jose, Calif.). Isotype-matched nonspecific antibodies were used as negative controls. The results of these binding studies are summarized in Table 2.

TABLE 2

| | | Binding to L-cells Expressing VCP-Deletion Mutants or WT L-cells | | | | | | |
|---|---|---|---|---|---|---|---|---|
| mAb | Epitope | SCR1-2 | SCR2-3 | SCR3-4 | SCR1-3 | SCR2-4 | SCR1-4 | WT |
| 5A10 | SCR1 | +++ | 0 | 0 | +++ | 0 | +++ | 0 |
| 6E5 | SCR1 | +++ | 0 | 0 | +++ | 0 | +++ | 0 |
| 3D9 | SCR2 | +++ | +++ | 0 | +++ | +++ | +++ | 0 |
| 6C4 | SCR2 | +++ | +++ | 0 | +++ | +++ | +++ | 0 |
| 2F10 | SCR3 | 0 | +++ | +++ | +++ | +++ | +++ | 0 |
| 5E7 | SCR3 | 0 | +++ | +++ | +++ | +++ | +++ | 0 |
| 1G1 | SCR4 | 0 | 0 | +++ | 0 | +++ | +++ | 0 |
| 5A1 | SCR4 | 0 | 0 | +++ | 0 | +++ | +++ | 0 |
| 5E1 | SCR4 | 0 | 0 | +++ | 0 | +++ | +++ | 0 |
| Irrelevant Monoclonal Antibody | n/a | 0 | 0 | 0 | 0 | 0 | 0 | 0 |

WT = wild-type. +++ indicates that the monoclonal antibody bound to the chimeric receptor expressed by the cell. 0 indicates that no binding occurred.

Detection of SPICE by mAbs using competitive ELISA. All nine mAbs detected rVCP by enzyme-linked immunosorbent assay (ELISA) (Table 3). To determine the minimum antibody concentration necessary for competitive ELISAs, each mAb was first diluted from 10 to 0.015 µg/mL and tested against VCPhis in an indirect ELISA using biotin-SP-conjugated goat anti-mouse IgG (1:5000; Jackson Immunoresearch), avidin-peroxidase (1:400; Sigma) and the Protein Detector ELISA Kit (KPL). Thereafter, 50 µL of 3 µg/mL of VCPhis was coated on a microtiter plate. Concurrently, each mAb (0.3 µg/mL) was incubated for 30 min with varying amounts of SPICEhis such that the SPICEhis:mAb molar ratios were either 1:1, 2:1, 3:1, 4:1, 5:1, 10:1, or 20:1. The microtiter plates containing VCPhis were then incubated with 50 µL of the SPICEhis/mAb solutions for 1 hour, followed by the secondary antibody described above. Loss of VCPhis-binding represented competitive binding by SPTCEhis. The results of this analysis are shown in Table 3.

TABLE 3

| mAb | VCP-binding | SPICE-binding |
|---|---|---|
| 5A10 | +++ | +++ |
| 6E5 | +++ | 0 |
| 3D9 | +++ | 0 |
| 6C4 | +++ | 0 |
| 2F10 | +++ | 0 |
| 5E7 | +++ | +++ |
| 1G1 | +++ | +++ |
| 5A1 | +++ | 0 |
| 5E1 | +++ | 0 |
| Irrelevant Monoclonal Antibody | 0 | 0 |

EXAMPLE 3

C3b and C4b Degradation

C3b or C4b degradation in the presence of SPICE and factor I. Cofactor activity was measured by incubating C3b or C4b with each cofactor at 37° C. Samples were removed at 0, 4, and 24 hours as indicated. Nine µg of C3b and C4b (Advanced Research Technologies (ART), San Diego, Calif.) were incubated with 3 µg of factor I (ART), and 6 µg of VCPhis, SPICEhis, factor H (ART) or soluble CR1 (sCR1; Novartis Pharmaceutical, Hanover, N.J.) in a total volume of 33 µL at 37° C. as previously described (Sahu, et al. (1998) J. Immunol. 160:5596–5604). Ten µL were removed at 0, 4, and 24 hours, mixed with sample buffer containing 2-mercaptoethanol (2-ME; BioRad, Hercules, Calif.), boiled 2 minutes, and separated by electrophoresis on a 9% SDS-PAGE. C3b and C4b cleavage products were visualized by staining the gel with Coomassie blue.

Rate of cofactor activity of SPICEhis, VCPhis and sCR1. Kinetic experiments were performed to compare the rate of cofactor activity at limiting concentrations of recombinant factors. C3b and C4b were incubated with factor I (13 µM) and 0.65 µM of SPICEhis, VCPhis, or sCR1 in a total volume of 66 µL at 37° C. Ten µL samples were removed at time intervals indicated and subjected to electrophoresis. Coomassie-stained gels were scanned for densitometric analysis using transmissive spectrophotometer (Model 355A, Molecular Dynamics, Sunnyvale, Calif.) and analyzed using the ImageQuant 3.2 Software (Molecular Dynamics). Reported values represent optical density (O.D.) relative to the original sample of the C3bα' or C4bα' chains. Experiments were performed 5 times with reproducible results obtained in all cases.

EXAMPLE 4

Inhibition of SPICE or VCP Cofactor Activity Using Anti-SPICE/VCP mAbs

The effect of SPICE/VCP mAb on cofactor activity was also examined. SPICE and VCP were pre-incubated with 0.5–3.0 molar equivalents of each mAb prior to the addition of C3b or C4b and factor I. SPICEhis reactions were stopped at 20 and 50 minutes for C3b and C4b, respectively. VCPhis reactions were stopped at 60 and 150 minutes for C3b and C4b, respectively. Degradation products were separated by 9% SDS-polyacrylamide gel electrophoresis, visualized using Coomassie blue and the gels were scanned for densitometric analysis using a transmissive spectrophotometer using well-known methods. Percent inhibition of a monoclonal antibody on cofactor function of VCP or SPICE was calculated as the O.D. of the α' chain band at each monoclonal antibody concentration compared to the O.D. of the α' chain band when no VCP or SPICE was added.

EXAMPLE 5

Species Preferences of SPICE

Complement-mediated hemolysis was evaluated by determining the highest dilution of human, dog, guinea pig, and baboon sera that resulted in 100% hemolysis of antibody-sensitized sheep erythrocytes (EA) or unsensitized rabbit erythrocytes (Er; $1\times10^8$/mL GVB$^{++}$; ART), respectively (Kitamura, H. Interspecies incompatibilities of complement factors and regulators, 564, Springer-Verlag, Berlin, 1998) at 37° C. Thereafter, the sera was serially diluted in U-bottom polypropylene 96-well plates (Corning, Inc., Corning, N.Y.) until no hemolysis was detected. Reactions were stopped after 1 hour with PBS (180 μL/well). Maximum hemolysis was obtained by the addition of water instead of PBS. Plates were centrifuged and 100 μL of supernatant was read at 405 nm. Serum heated to 56° C. for 30 minutes established background hemolysis.

To determine the influence of various CRPs on complement-mediated hemolysis of EA or Er, 25 μL of serially-diluted serum was added, followed by 25 μL of 0.1–0.25 mg/mL CRP or PBS, and 50 μL of erythrocytes ($1\times10^8$/mL in GVB$^{++}$). Reported values represent percent of maximum hemolysis for CRP-treated wells relative to PBS-treated wells at identical serum dilutions. All experiments were performed between 3 and 10 times, and reproducible results were obtained in all cases.

EXAMPLE 6

Detection and Differentiation of Orthopoxviruses in Serum/Plasma Using Restriction Fragment Length Polymorphism Analysis Using heparin for anticoagulation, mice were bled from the eye or tail vein and the blood was separated into plasma and blood cells by centrifugation. DNA from plasma (100 μl) was purified using the High Pure Viral Nucleic Acid Kit (Roche, Indianapolis, Ind.) according to the manufacturer's instructions.

Using primer pairs flanking the terminal regions of the VCP and SPICE genes (Sense Primer 1 (5'Bgl SCR1): 5'-GAA GAT CTT TGT ACT ATT CCG TCA CGA CCC ATT AAT-3', SEQ ID NO:11; or Sense primer 2: 5'-AAA TCG TAT TGT GAA TTA GGA TCT ACT GGA TCT ATG G-3', SEQ ID NO:13; in combination with Antisense Primer (5' Nhe1 SCR4): 5'-CTA GCT AGC GCG TAC ACA TTT TGG AAG TTC CGG CTT-3', SEQ ID NO:12) a standard PCR reaction was performed on serum-purified viral DNA. Thirty μL of purified DNA was added to 34 μL of water and 36 μL of master mix (8 μL Sense Primer, 8 μL Antisense Primer, 4 mL MgCl$_2$ (Roche, Indianapolis, Ind.), 10 μL 10×PCR Buffer, 2 dNTPs, 0.5 μL Taq Polymerase (Invitrogen, Carlsbad, Calif.), and 3.5 μL water). DNA was amplified for 50 cycles (1 minute at 95° C., 1 minute at 65° C., 1 minute at 72° C.), extended for 5 minutes at 72° C., and stored at 4° C.

Endonuclease digestion with SspI was performed using standard methods. DNA fragments were resolved by gel electrophoresis using 1 to 1.5% agarose gels in TAE buffer.

To test the sensitivity of the PCR step, various volumes (0.001 μL–4 μL) of vaccinia virus ($1\times10^8$ pfu/mL) were added to 80 μL of serum/plasma and the VCP fragment was amplified as described herein. Resolution by gel electrophoresis showed a single VCP fragment was amplified from all volumes tested.

EXAMPLE 7

Inhibition of Vaccinia Virus Infection

Briefly, 4–6 week-old female BALB/c mice were divided into three groups based on the immunotherapy and vaccinia (or no virus) injections received. The experimental group received an intraperitoneal injection consisting of a cocktail of 50 μg of each anti-VCP monoclonal antibody on day −1 and +2 and an intradermal inoculation of $5\times10^7$ pfu of vaccinia virus WR (ATCC #VR-1354) in each hind footpad on day 0. The irrelevant antibody control group received mouse anti-biotin monoclonal antibody (450 μg) on day −1 and day +2 and $5\times10^7$ pfu vaccinia in each hind footpad on day 0. The no virus control group received anti-biotin monoclonal antibody (450 μg) on day −1 and day +2 and PBS, pH 7.4, injections (no virus) in each hind footpad on day 0. The experiment was repeated three times with consistent results. In total, 15 mice were in the experimental group, 13 mice were in the irrelevant monoclonal antibody control group, and 8 mice were in the no virus control group. To confirm absorption of the anti-VCP monoclonal antibodies in the experimental group, indirect ELISA was performed with the serum from mice on day 2 using VCPhis-coated microtiter plates.

Footpad thickness of each hindfoot was measured using an engineer's micrometer (Miller, et al. (1995) *Cell. Immunol.* 162:326) by the same individual to eliminate interobserver variability. The observer was blinded to the contents of the inocula. The average of the two hindfoot measurements for each day was recorded and plotted.

Analysis of footpad measurements was aimed at comparing the entire longitudinal response between groups (experimental group, irrelevant monoclonal antibody control group, and no virus control group) and between three experiments. Analysis was performed using the SAS statistical package, Version 8.2. To test group difference, random effects regression models were used that allow for the correlation of repeated observations on the same animal over time. Variability among animals was assumed in the overall level of response, as was variability in levels of responses across experiments. Agreement of results across experiments was observed. Results are presented as differences in mean footpad thickness between the experimental and irrelevant monoclonal antibody control groups for each day in the each experiment, expressed as a percentage of the irrelevant monoclonal antibody control group mean; these differences were significant as defined by $p<0.05$.

What is claimed is:

1. A method for treating variola or vaccinia virus infections comprising administering an effective amount of at least one isolated antibody which specifically binds SPICE or VCP so that signs or symptoms of variola or vaccinia virus are prevented or reduced.

2. A method for treating variola or vaccinia virus infections comprising administering an effective amount of at least one isolated antibody which specifically binds SPICE or VCP and a pharmaceutically acceptable carrier so that signs or symptoms of variola or vaccinia virus are prevented or reduced.

* * * * *